(12) United States Patent
Wisse et al.

(10) Patent No.: US 8,597,370 B2
(45) Date of Patent: Dec. 3, 2013

(54) ARTIFICIAL HAND

(75) Inventors: Martijn Wisse, Oegstgeest (NL); Freerk Wilbers, Delft (NL); Cory Meijneke, Utrecht (NL)

(73) Assignee: Lacquey B.V., Delft (NL)

( * ) Notice: Subject to any disclaimer, the term of this patent is extended or adjusted under 35 U.S.C. 154(b) by 25 days.

(21) Appl. No.: 13/341,062

(22) Filed: Dec. 30, 2011

(65) Prior Publication Data

US 2012/0150323 A1 Jun. 14, 2012

Related U.S. Application Data

(63) Continuation of application No. PCT/NL2010/050427, filed on Jul. 5, 2010.

(30) Foreign Application Priority Data

Jul. 9, 2009 (NL) .................................. 2003156

(51) Int. Cl.
*A61F 2/54* (2006.01)
(52) U.S. Cl.
USPC .................. 623/64; 623/24; 901/38; 294/213

(58) Field of Classification Search
USPC ........................ 623/24, 57–64; 294/104, 106; 901/31–39; 295/213
See application file for complete search history.

(56) References Cited

U.S. PATENT DOCUMENTS

| 5,762,390 | A  | * | 6/1998 | Gosselin et al. | ............... 294/106 |
|---|---|---|---|---|---|
| 6,358,285 | B1 |  | 3/2002 | Chen |  |
| 6,423,099 | B1 |  | 7/2002 | Iversen et al. |  |
| 2004/0117034 | A1 |  | 6/2004 | Weir et al. |  |
| 2011/0257765 | A1 | * | 10/2011 | Evans et al. | ..................... 623/24 |

* cited by examiner

*Primary Examiner* — Bruce E Snow
(74) *Attorney, Agent, or Firm* — Jeffrey D. Myers; Peacock Myers, P.C.

(57) ABSTRACT

Artificial hand suitable for robotic applications or as a prosthesis, comprising a frame with a thumb and at least two fingers, and having a motor drive for adjusting the thumb and the fingers with respect to the frame, wherein the motor drive has a housing and an axle which is rotatably positioned within the housing, and wherein the housing is mounted in a first bearing supported by the frame to enable that the housing may rotate with regard to the frame, and that the thumb and fingers are drivingly connected with the housing and the axle respectively.

6 Claims, 4 Drawing Sheets

ARTIFICIAL HAND

CROSS-REFERENCE TO RELATED APPLICATIONS

This application is a continuation application of International Patent Application Serial No. PCT/NL2010/050427, entitled "Artificial Hand", to Lacquey B. V., filed on Jul. 5, 2010, which is a continuation of Netherlands Patent Application Serial No. 2003156 entitled "Artificial Hand", to Lacquey B. V., filed on Jul. 9, 2007, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to an artificial hand suitable for robotic applications or as a prosthesis, comprising a frame with a thumb and at least two fingers, and having a motor drive for adjusting the thumb and the fingers with respect to the frame.

2. Description of Related Art

Such an artificial hand is described in the Dutch patent application NL-A-2,001,847, which is yet to be published.

The artificial hand that is described in said patent application is of quite a complicated construction in order to meet the objective of being under actuated, and results into an operation of the artificial hand in which it automatically adapts to the circumstances and shape of an object which it is intended to grip. The forces to be applied on said object with the thumb and fingers of the artificial hand are of equal strength albeit with opposite directions, which means that in operation the artificial hand as a whole will not move except for the movement of the thumb and fingers.

BRIEF SUMMARY OF THE INVENTION

It is an object of the invention to further develop the artificial hand of NL-A-2,001,847 into a more robust construction, which is easier to manufacture and which is better suited to work under stressful conditions such as humidity, dust, and high temperatures.

The object of the invention and other advantages which will become apparent from the following disclosure, are attained with the artificial hand in accordance with one or more of the appended claims.

BRIEF DESCRIPTION OF THE SEVERAL VIEWS OF THE DRAWINGS

The invention will hereinafter be further elucidated with reference to an exemplary embodiment of the artificial hand according to the invention that is not limiting the appended claims. In the drawings:

Wherever in the figures the same reference numerals are applied, these numerals refer to the same parts.

DETAILED DESCRIPTION OF THE INVENTION

Figure 1:
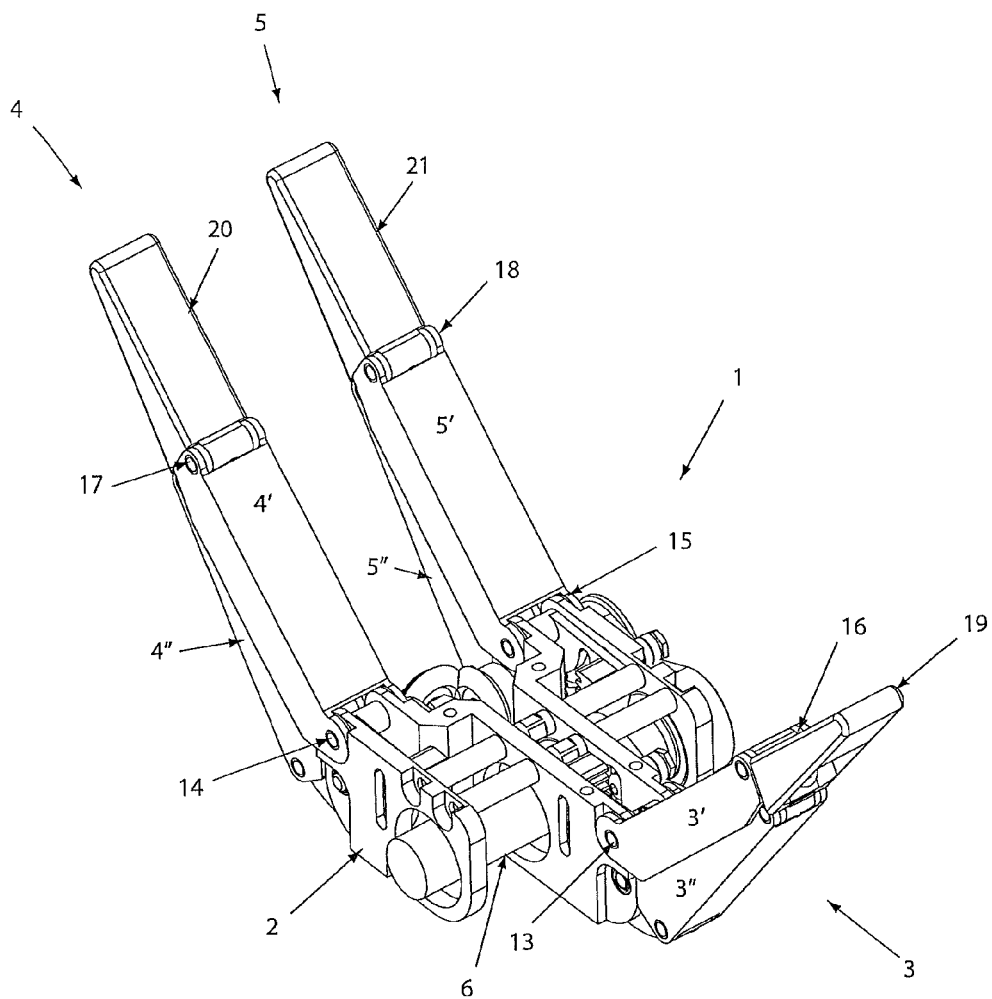
FIG. 1 shows an isometric view of the artificial hand of the invention.

In a first aspect of the invention, the artificial hand is characterized in that the motor drive has a housing and an axle which is rotatably positioned within the housing, that the housing is mounted in a first bearing supported by the frame to enable that the housing may rotate with regard to the frame, and that the thumb and fingers are drivingly connected with the housing and the axle respectively.

With this construction it is the motor drive itself that is used to distribute the driving forces to the thumb and fingers respectively according to the load on said thumb and fingers, without need to apply an additional force distribution mechanism, such as bevel gears, planetary gears, cables and pulleys and other systems that are commonly used in the prior art for the transfer of the driving forces from the motor drive to the thumb and fingers.

Preferably the axle is mounted in a second bearing supported by the frame. This secures that an even load distribution of the motor drive to the frame can be realized, since the load forces are in part taken up by the bearing supporting the axle, and in part by the bearing supporting the housing of the motor drive.

A further desirable feature is that the two fingers have drive-axles that are positioned coaxially and in line with each other, with an inter-positioned differential to allow that a driving torque from the motor drive is distributed to the respective fingers in accordance with their load during use of the hand.

This differential is embodied without housing by the arrangement that the drive axles of the fingers are embodied as hollow tubes, in which a central shaft is housed that supports a planetary wheel of the differential.

The artificial hand according to the invention is preferably embodied such that the thumb and fingers are connected to the frame with hinges, and are drivingly connected with their respective driving axles through rack-and-pinion drives that are placed eccentric with respect to the hinges. This is an effective way of converting the rotational motion of the motor drive into a driving motion for the thumb and fingers, whereby the rack is embodied as a quarter circle element with internal toothing that is connected to the parts of the thumb and fingers near to the frame.

In another aspect of the invention the artificial hand is embodied such that each of the thumb and fingers has two U-bars, the open faces of which are facing each other, whereby the legs of one U-bar fit between the legs of the other U-bar, and wherein said two U-bars embody the opposite links of a four-bar mechanism, whereby the first of the remaining links is formed by the rack of the rack-and-pinion near the connection of the U-bars to the frame, and a second of the remaining links is formed by the distal phalanges of the thumb and fingers. This construction is helpful in realizing a proper drive of the thumb and fingers, and furthermore it provides a complete closure of said thumb and fingers providing an effective bar against ingress of particles.

Figure 2:
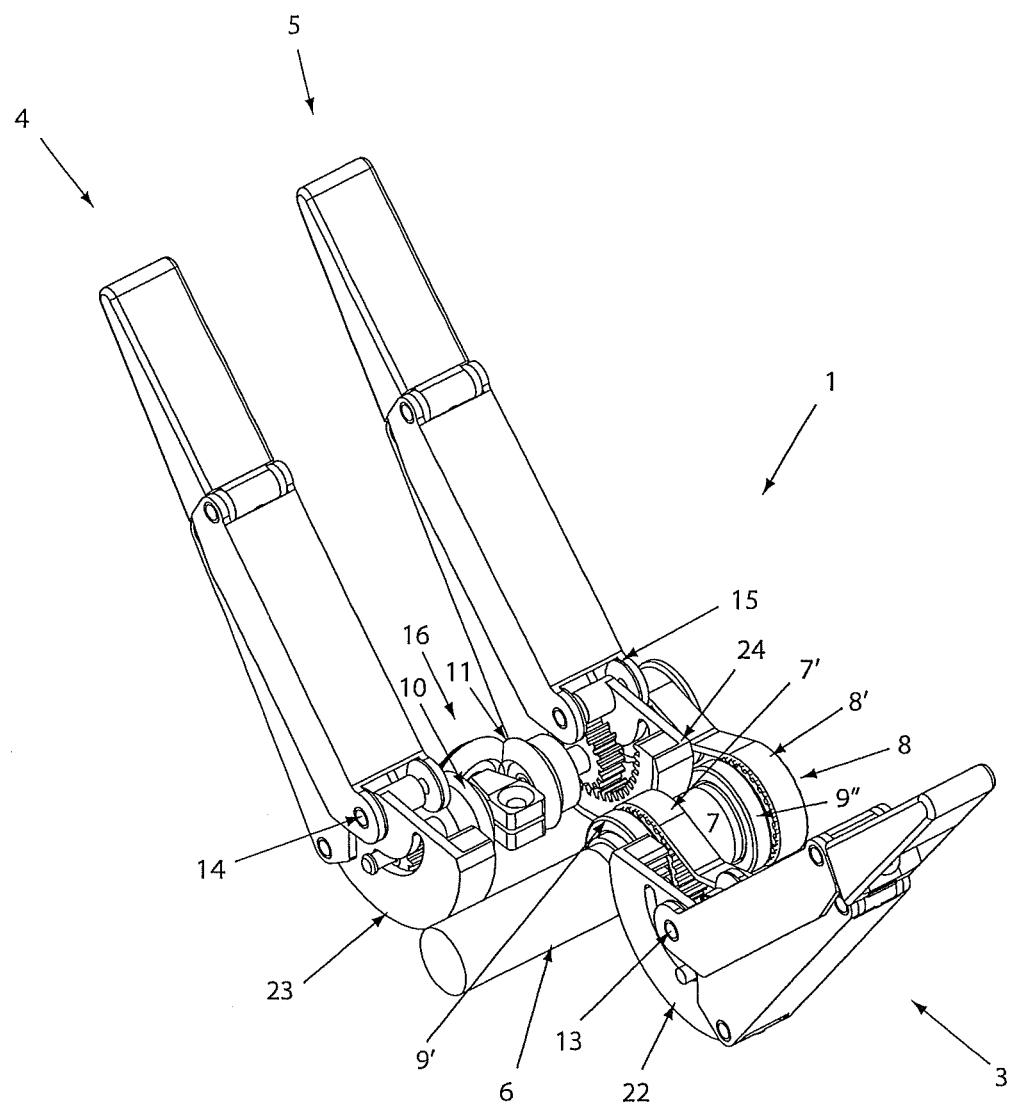
FIG. 2 shows the artificial hand of FIG. 1 without the frame.

With reference first to FIG. 1 and FIG. 2, the artificial hand of the invention is indicated with reference numeral 1. FIG. 1 shows that the artificial hand 1 is embodied with a frame 2, and further that it has a thumb 3 and in the shown case also two fingers 4, 5.

FIG. 1 and more clearly FIG. 2 show that the artificial hand 1 has a motor drive 6 which is used for adjusting the thumb 3 and fingers 4, 5.

Figure 3:
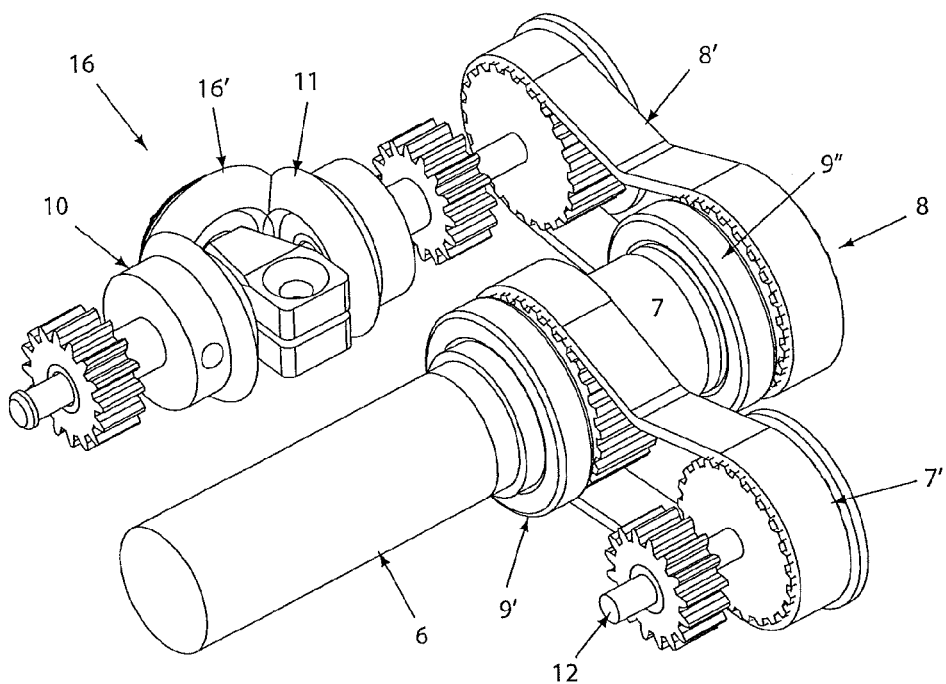
FIG. 3 shows the drive train of the artificial hand of the invention.

In accordance with the invention FIG. 2 and more clearly FIG. 3 show that the motor drive 6 has a housing 7 and an axle 8. The axle 8 is in a known manner rotatably positioned within the housing 7. According to the invention however the housing 7 is mounted in a first bearing 9' that is supported by the frame 2, which enables that the housing 7 can rotate with respect to the frame 2. Likewise the axle 8 is mounted in a second bearing 9" that is also supported by the frame 2. The load of the motor drive 6 with respect to the frame 2 is thus evenly distributed.

FIG. 2 and FIG. 3 further show that the thumb 3 and fingers 4, 5 are drivingly connected with the housing 7 and the axle 8 respectively by means of the belts 7' and 8'.

With reference further to FIG. 3 which shows the drive train without the driven thumb 3 and fingers 4, 5, it is shown that the fingers 4, 5 have drive axles 10, 11 that are positioned coaxially and in line with each other, with an inter-positioned differential 16 to allow that a driving torque from the motor drive 6 is distributed to the respective fingers 4, 5 in accordance with the loads experienced by the said fingers 4, 5 during use of the artificial hand 1 of the invention.

The said drive axles 10, 11 are preferably embodied as hollow tubes that accommodate a central shaft that is rotatably positioned therein and that supports a planetary wheel 16' of the differential 16. The differential 16 per se thus can be embodied without housing.

Figure 4:
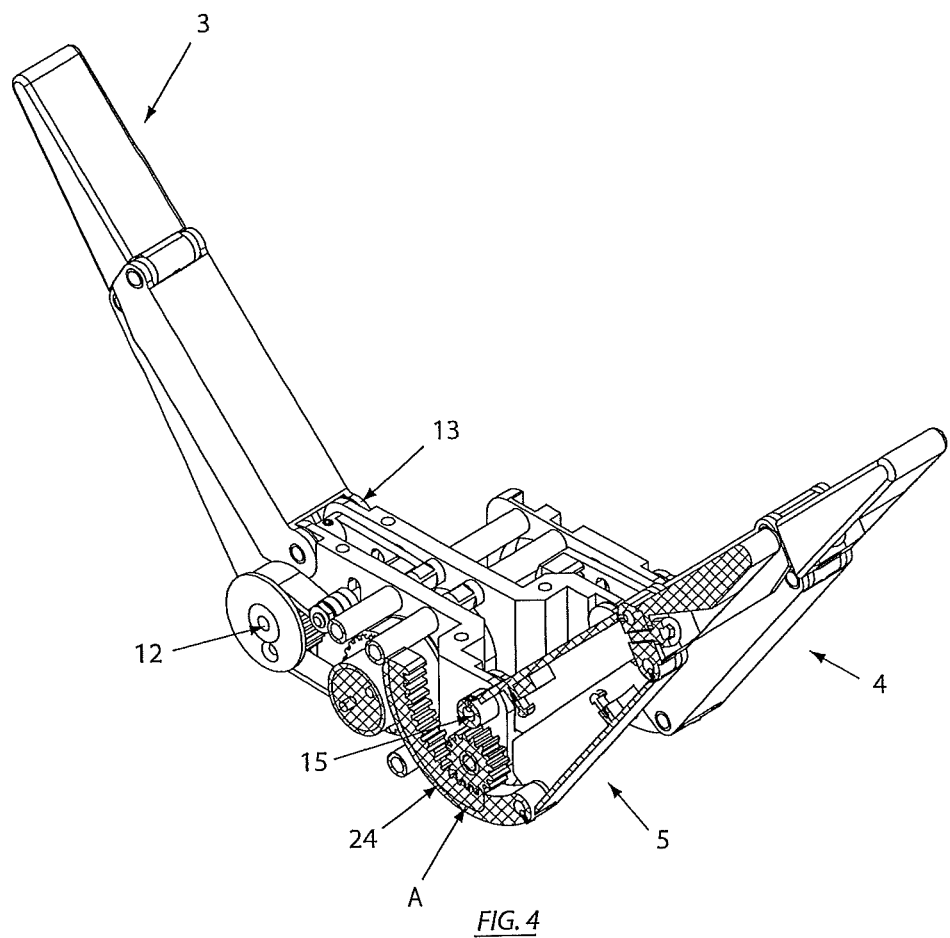
FIG. 4 shows a worked-open oblique side-view of the artificial hand of the invention.

With reference again to FIGS. 1 and 2 it is shown that the thumb 3 and fingers 4, 5 are connected to the frame 2 with hinges 13, 14, 15. As can be best seen in FIG. 2 the thumb 3 and fingers 4, 5 are drivingly connected with their respective driving axles 10, 11, 12 through rack-and-pinion drives that are placed eccentric with respect to the hinges 13, 14, 15. A good view at the rack-and-pinion drive of finger 5 is shown in FIG. 4, and is indicated with arrow A showing that this drive is eccentric with respect to the hinge 15.

It is further remarked that in a particular aspect of the invention both the thumb 3 and the respective fingers 4, 5 comprise two U-bars 3', 3", 4', 4", 5', 5" (see FIG. 1). The open faces of said U-bars face each other so as to embody the thumb and fingers as a complete enclosure of an inner void. To this end the legs of the U-bars 3", 4", 5" fit between the legs of the cooperating U-bars 3', 4', 5'.

With this construction the two cooperating U-bars 3', 3", 4', 4", 5', 5" embody a first set of the opposite links of a four-bar mechanism, whereby a first of the remaining links is near the connection provided by the hinges 13, 14, 15 of the U-bars to the frame 2, and is formed by the racks 22, 23, and 24 (see FIG. 2) of the concerning rack-and-pinion drives of the thumb 3, and fingers 4, 5. A second of the remaining links is at the joint 16, 17, 18 of the said U-bars 3', 3", 4', 4", 5', 5" and is formed by the phalanges 19, 20, 21 of the thumb 3 and fingers 4, 5 distant from the frame 2. This is clearly shown in FIG. 1.

It is expressly remarked that the above given elucidation with reference to the drawing is not limiting the appended claims, and that this elucidation is only intended to remove any possible ambiguity that may exist in the wording of the claims.

What is claimed:

1. Artificial hand suitable for robotic applications or as a prosthesis,
    comprising a frame with a thumb and at least two fingers, and having a motor drive for adjusting the thumb and the fingers with respect to the frame,
    wherein the motor drive has a housing and an axle which is rotatably positioned within the housing,
    the housing is mounted in a first bearing supported by the frame to enable that the housing may rotate with regard to the frame, and
    the thumb and fingers are drivingly connected with the housing and the axle respectively.

2. Artificial hand according to claim 1, wherein the axle is mounted in a second bearing supported by the frame.

3. Artificial hand according to claim 1, wherein the two fingers have drive-axles that are positioned coaxially and in line with each other, with an inter-positioned differential to allow that a driving torque from the motor drive is distributed to the respective fingers in accordance with their load during use of the hand.

4. Artificial hand according to claim 3, wherein the drive axles of the two fingers are embodied as hollow tubes housing a central shaft that supports a planetary wheel of the differential.

5. Artificial hand according to claim 1, wherein the thumb and fingers are connected to the frame with hinges, and are drivingly connected with their respective driving axles through rack-and-pinion drives that are placed eccentric with respect to the hinges.

6. Artificial hand according to claim 1, wherein the thumb and fingers has two U-bars, the open faces of which are facing each other, whereby the legs of one U-bar fit between the legs of the other U-bar, and wherein said two U-bars embody opposite links of a four-bar mechanism, whereby a first of the remaining links is near the connection of the U-bars to the frame and is formed by the respective racks of said rack-and-pinion drives, and a second of the remaining links is formed by the distal phalanges of the thumb and fingers that are distant from the frame.

* * * * *